United States Patent [19]

Davis et al.

[11] Patent Number: 5,384,333
[45] Date of Patent: Jan. 24, 1995

[54] BIODEGRADABLE INJECTABLE DRUG DELIVERY POLYMER

[75] Inventors: Patricia A. Davis; Scott Cousins, both of Miami, Fla.

[73] Assignee: University of Miami, Miami, Fla.

[21] Appl. No.: 852,948

[22] Filed: Mar. 17, 1992

[51] Int. Cl.$^6$ ............ A01N 25/26; A61K 37/22; A61K 9/50
[52] U.S. Cl. ............... 514/772.3; 424/417; 424/450; 424/489; 424/501; 264/4.1; 264/4.33; 264/4.4; 523/500
[58] Field of Search ............ 424/405, 408, 417, 418, 424/420, 427, 428, 450, 78.04, 78.38, 489, 501; 523/500; 264/4.1, 4.33, 4.4; 428/402.21; 514/772.3

[56] References Cited

U.S. PATENT DOCUMENTS

| | | | |
|---|---|---|---|
| 3,219,527 | 11/1965 | Gurney | 424/435 |
| 3,328,246 | 6/1967 | Gottfried et al. | 514/558 |
| 3,520,949 | 7/1970 | Shepherd et al. | 525/426 |
| 3,696,811 | 10/1972 | Chen | 602/56 |
| 3,887,699 | 6/1975 | Yolles | 424/477 |
| 3,931,678 | 1/1976 | O'Sullivan et al. | 433/228.1 |
| 3,981,303 | 9/1976 | Higuchi et al. | 424/428 |
| 3,986,510 | 10/1976 | Higuchi et al. | 424/428 |
| 3,995,635 | 12/1976 | Higuchi et al. | 424/427 |
| 4,161,948 | 7/1979 | Bichon | 602/58 |
| 4,188,373 | 2/1980 | Krezanoski | 514/11 |
| 4,201,210 | 5/1980 | Hughes et al. | 424/428 |
| 4,202,880 | 5/1980 | Fildes et al. | 424/433 |
| 4,217,898 | 8/1980 | Theeuwes | 424/433 |
| 4,450,150 | 5/1984 | Sidman | 424/1.1 |
| 4,474,751 | 10/1984 | Haslam et al. | 514/11 |
| 4,474,752 | 10/1984 | Haslam et al. | 424/85.4 |
| 4,474,753 | 10/1984 | Haslam et al. | 424/78.06 |
| 4,491,479 | 1/1985 | Lauchenauer | 106/15.05 |
| 4,568,536 | 2/1986 | Kronenthal et al. | 424/435 |
| 4,570,629 | 2/1986 | Widra | 604/304 |
| 4,582,640 | 4/1986 | Smestad et al. | 530/35 |
| 4,650,665 | 3/1987 | Kronenthal et al. | 424/435 |
| 4,677,139 | 6/1987 | Feinmann et al. | 128/888 |
| 4,715,369 | 12/1987 | Suzuki et al. | 604/49 |
| 4,772,470 | 9/1988 | Inoue et al. | 424/435 |
| 4,774,227 | 9/1988 | Piez et al. | 514/21 |
| 4,793,336 | 12/1988 | Wang | 604/304 |
| 4,853,224 | 8/1989 | Wong | 424/427 |
| 4,863,457 | 9/1989 | Lee | 604/891.1 |
| 4,865,846 | 9/1989 | Kaufman | 424/428 |
| 4,882,150 | 11/1989 | Kaufman | 424/428 |
| 4,938,763 | 7/1990 | Dunn et al. | 604/891.1 |
| 4,975,271 | 12/1990 | Dunn et al. | 424/49 |
| 4,997,656 | 3/1991 | Shikinami et al. | 424/449 |
| 5,013,553 | 5/1991 | Southard et al. | 514/279 |
| 5,077,049 | 12/1991 | Dunn et al. | 424/426 |

FOREIGN PATENT DOCUMENTS 9200718 1/1992 WIPO.

OTHER PUBLICATIONS

Niekraszewicz, "Resorbable fibers and polymers for medicine II Synthesis of copoly(ester ethers)", Wlokra Chem, 16(2), 153"61, 1990.

Sakurai et al, "Water-soluble high molecular weight polymerized drug preparation", European Pat. Appl., EP397307A2, 14 Nov. 1990.

Yokoyama et al, "Polymer micelles as novel drug carriers: Adriamycin-conjugated block copolymer", J. Controlled Release, 11(1-3) 269-78, 1990.

Cerrai et al, "Polyether-polyester block . . . poly(ethylene glycol)", Polymer, 1989, vol. 30, Feb., pp. 338-343.

*Primary Examiner*—Thurman K. Page
*Assistant Examiner*—C. Azpuru
*Attorney, Agent, or Firm*—Cushman, Darby & Cushman

[57] ABSTRACT

A bio-injectable drug composition which provides long term drug release. The drug composition is made up of a pharmaceutically active agent in a biodegradable polymer matrix, where the polymer matrix is a solid at temperatures in the range 20° to 37° C. and is flowable at temperatures in the range 38° to 52° C.

10 Claims, No Drawings

BIODEGRADABLE INJECTABLE DRUG DELIVERY POLYMER

The present invention relates to a biodegradable injectable drug delivery polymer system which provides an improved medium for the administration of sustained release drugs to the human body, especially to the eye.

BACKGROUND OF THE INVENTION

Current technology for the intraocular introduction of drugs consists of either bulky, implantable drug delivery devices or injectable microspheres which contain drugs. These delivery systems suffer from drawbacks which make them undesirable for general clinical use. In particular, implantation of bulky ocular implants requires surgery, with all its attendant risks. Microspheres suffer from the drawback that they migrate within the eye, either into the visual axis, or into adjacent tissue sites.

Some patents which exemplify the current state of this technology, none of which have been developed into clinically useful devices, are discussed below. In order to discuss these devices, it is necessary to clarify some terms which are used in these patents.

The literature uses the term "ocular" in a confusing manner, improperly categorizing intraocular devices with extra-ocular devices. "Ocular" should be referenced using these terms which reflect anatomy, physiology and the invasiveness of the particular method.

As used in this application, "extraocular" refers to the ocular surface and the (external) space between the eyeball and the eyelid. Example of "extraocular" regions include the eyelid fornix or cul-de-sac, the conjunctival surface and the corneal surface. This location is external to all ocular tissue and an invasive procedure is not required to access this region. Extraocular devices are generally easily removable, even by the patient. Examples of extraocular systems include contact lenses and "topically" applied drops.

The following patents disclose extraocular systems which are used to administer drugs to the extraocular regions.

Higuchi et al. discloses in U.S. Pat. Nos. 3,981,303, 3,986,510 and 3,995,635, a biodegradable ocular insert which contains a drug. The insert can be made in three different shapes for retention in the cul-de-sac of the eyeball, the extraocular space between the eyeball and the eyelid. Several common biocompatible polymers are disclosed as suitable for use in fabricating this device. These polymers include zinc alginate, poly (lactic acid), poly (vinyl alcohol), poly (anhydrides) and poly (glycolic acid). The patents also disclose membrane coated devices with reduced permeation to the drug and hollow chambers holding the drug formulation.

British Patent 1,529,143 discloses a crescent-shaped drug releasing ocular insert. This insert is placed and retained in the upper fornix above the upper eyelid and the eyeball. This is another extraocular device.

Hughes et al., U.S. Pat. No. 4,201,210 discloses an extraocular device for use in animal eyes. This device is a controlled release system in the shape of a ring.

Theeuwes, U.S. Pat. No. 4,217,898, discloses microporous reservoirs which are used for controlled drug delivery. These devices are placed extraocularly in the ocular cul-de-sac. Four device shapes are disclosed. Among the polymer systems of interest include poly (vinylchloride)-co-poly (vinyl acetate) copolymers.

Kaufman discloses in U.S. Pat. Nos. 4,865,846 and 4,882,150 discloses an ophthalmic drug delivery system which contains at least one bio-erodible material or ointment carrier for the conjunctival sac. Suitable drugs which are used in this delivery system include pilocarpine. The patent discloses polymer systems, such as, poly (lactide), poly (glycolide), poly (vinyl alcohol) and cross linked collagen, as suitable delivery systems.

Brightman et al., U.S. Pat. No. 4,474,751, discloses a biodegradable ocular insert for the controlled delivery of ophthalmic material. This insert is an extraocular insert which is attachable to the third eyelid in animal eyes. The insert is used for the controlled delivery of medication.

The preceding patents all relate to extraocular systems, as the term is defined above.

Intraocular systems are those systems which are suitable for use in any tissue compartment within, between or around the tissue layers of the eye itself. These locations include subconjunctival (under the ocular mucous membrane adjacent to the eyeball), orbital (behind the eyeball), and intracameral (within the chambers of the eyeball itself). In contrast to extraocular systems, a surgical procedure consisting of injection or implantation is required to access these regions. This requires a direct invasion of the integrity of the eye during implantation, and would require major surgery to remove. The following patents disclose intraocular devices.

Wong, U.S. Pat. No. 4,853,224, discloses microencapsulated drugs for introduction into the chamber of the eye. Polymers which are used in this system include polyesters and polyethers. Examples of drugs which can be delivered by this system include 5-fluorouracil, pilocarpine and acyclovir.

Lee, U.S. Pat. No. 4,863,457, discloses a biodegradable device which is surgically implanted intraocularly for the sustained release of therapeutic agents. The device is designed for surgical implantation under the conjunctiva (mucous membrane of the eyeball). The device is disc-shaped with a protruding "handle" for suture fixation.

Krezancaki, U.S. Pat. No. 4,188,373, discloses a pharmaceutical vehicle which gels at human body temperature. This vehicle is an aqueous suspension of the drug and gums or cellulose derived synthetic derivatives. The suspension remains liquid below 30° C. (room temperature), and only undergoes a sol-gel transformation in the temperature range 25°–40° C. Thus, in this system, a covalent chemical interaction is taking place within the site of injection.

Haslam et al. discloses in U.S. Pat. Nos. 4,474,751 and 4,474,752 a polymer-drug system which is liquid at room temperature and gels at body temperature. Suitable polymers used in this system include polyoxyethylene and polyoxy propylene. Suitable drugs include 5-FU, gentamycin, triamcinolone, and acyclovir. This system requires an intraocular, temperature dependent chemical polymerization reaction between the polymer components. This is fundamentally different from the concept of the present invention. U.S. Pat. No. 4,474,753 discloses the use of this system in a topical setting.

SUMMARY OF THE INVENTION

The present invention relates to novel biodegradable polymer systems called "meltamers" and their use to introduce pharmaceutically active agents into the body, especially into intraocular portions of the eye. The present polymer compositions can be introduced into the eye via injection, and thus avoid the need for surgical invasion of the eyeball itself. In addition, the present compositions avoid the need for covalent chemical reactions to take place within the eyeball. This offers a vastly simplified procedure compared to previous methods.

One aspect of the present invention is a drug delivery composition comprising a pharmaceutically active agent and a biodegradable polymer, wherein said biodegradable polymer is solid at temperatures in the range 20°-37° c. and is liquid in the temperature range 38°-52° C.

A further aspect of the present invention is a method of introducing a pharmaceutically active compound into the human body, the method comprising the steps of:

(a) forming a drug delivery composition which comprises a pharmaceutically active agent and a biodegradable polymer, wherein the biodegradable polymer is solid at temperatures in the range 20°-37° C. and is liquid at temperatures in the range 38°-52° C., wherein the drug delivery composition is formed by mixing the pharmaceutically active agent with the biodegradable polymer;

(b) liquefying the drug delivery system by heating to a temperature where it liquifies; and (c) injecting the liquid polymer into the body.

Other objects, features and characteristics of the present invention, as well as the methods of operation and functions of the related elements of the structure, and the combination of parts and economies of manufacture, will become more apparent upon consideration of the following detailed description and the appended claims with reference to the accompanying drawings all of which form a part of this specification, wherein like reference numerals designate corresponding parts in the various figures.

DETAILED DESCRIPTION OF THE PRESENTLY PREFERRED EXEMPLARY EMBODIMENT

The present invention provides a bio injectable drug delivery system and a method of introducing a drug into the body for sustained release.

The drug delivery system of the present invention comprises biodegradable drug delivery systems which include a drug containing polymer matrix which is solid at 20°-37° C. and is flowable, e.g. a liquid in the temperature range 38°-52° C. This system can be warmed to approximately 50° C., where it liquifies and injected into the portion of the body requiring treatment, where it resolidifies. No covalent reaction, setting or other clinical process is required, other than cooling. This allows all polymer/drug interactions to be pre-formulated in the laboratory prior to injection. This preformulation results in an injectable system which has excellent sustained drug release characteristics without the drawbacks of invasive surgery or chemical reactions. The polymer biodegrades completely and leaves no ghost or residue.

The present injectable delivery system provides an improved way of delivering drugs into the body. This provides the drugs in a form which allows sustained release of the drug compound into the body. Currently topical medicines or injections of soluble drugs are the only options for clinical use. These media have short half-lives.

The drug delivery polymer is not limited to the delivery of soluble or liquid drug formulations. For example, the polymer can be used as a matrix for stabilizing and retaining at the site of injection drug-containing microspheres, liposomes or other particulate-bound drugs. In addition, pharmacologically active proteins, such as growth factors, cytokines or other biological response modifying substances can be incorporated and delivered with this polymer system.

Significant problems are associated with the use of currently available technology for intraocular sustained released. These involve the use of bulky implants which require surgical implantation, and injectable microspheres which suffer from migration problems.

The present system provides the advantage that it is simple to use. A simple injection, for example, with an 25 gauge needle, is all that is required to introduce the drug delivery device into the eye. Once inside the eye, it solidifies by a simple cooling process. Then the solid polymer slowly degrades and releases the drug. No covalent chemical reactions are required, thus obviating problems which are related to different intraocular conditions which might arise due to different applications, prior surgery or concurrent disease. Furthermore the device dissolves completely and thus does not leave a ghost or residue which would require surgical removal.

Potential uses for the present invention include controlled delivery of drugs or active agents to the vitreous cavity of the eye for treating diseases such as complicated retinal detachment, CMV retinitis in AIDS and other conditions. The system could also be used for the sustained release of anti-metabolites subconjunctivally to prevent wound healing of a filtering bleb after laser glaucoma filtering surgery to control fibroblast proliferation. The system is also suitable for use in delivery of sustained release of antibiotics or anti-inflammatory drugs in the eye, for example after cataract surgery. Additionally, the present system is suitable for use in other parts of the body which require sustained drug therapy. Examples of these uses include intralesional therapy of cutaneous disorders, intra-articular delivery of agents and intracranial drug delivery. These uses are intended as illustrative and do not limit the scope of the present invention. Those skilled in the art may desire other uses for this system within the scope of the present invention.

A preferred use of the present invention is for the introduction of pharmaceutically active compounds into the intraocular region of the eye. However, the present drug delivery system should not be viewed as limited to intraocular use.

The present invention avoids the hazards of eye surgery to insert the drug delivery device and also avoids intraocular chemical reactions.

Any biodegradable polymer system which has the following characteristics is suitable for use in the biodegradable polymer matrix in the present system. Homopolymers, co-polymers, block co-polymers, waxes and gels which are: biodegradable, compatible with a variety of drugs; are solid at temperatures; between 20° and 37° C.; are liquid at 38°-52° C.; and have the capacity to melt and resolidify without additional chemical reactions at these temperatures and can be formed in laboratory and used without the need for further chemical interaction. The polymer matrix can be formed in the lab or production by any suitable means, and can be compounded with the drug by any means which allow the above requirements to be satisfied.

A preferred polymer system is a triblock copolymer. This block copolymer has the general formula:

A—B—A where A represents a hydrophobic polymer block and B represents a hydrophilic polymer. The biodegradable monomers and polymers are preferably linked through ester groups. Preferred hydrophobic polymers and oligomers include, but are not limited to units selected from polyglycolic acid, polyethylene terephthalate, polybutyl lactose, polycaprolactone, D-polylactic acid, L-polylactic acid, polyglytamic acid, poly-L-lysine and poly-L-aspartic acid.

Preferred hydrophilic polymers include polyethylene glycol, polypropylene glycol and poly vinyl alcohol.

A particularly preferred biodegradable polymer matrix is a triblock copolymer of poly caprolactone (PCL)—polyethylene glycol (PEG)-poly caprolactone. This polymer contains ester bonds which hydrolyze in a hydrophilic environment, such as the eye. This preferred polymer has the formula:

$H[O(CH_2)_5CO]_n—[OCH_2—CH_2O]_m—[OC(CH_2)_5O]_n—H$ where m is in the range 6.67 to 16.67 and n is in the range 4.65 to 17.54.

A particularly preferred embodiment of this polymer is the block copolymer of two units of poly caprolactone with a molecular weight of 2000 and one unit of polyethylene glycol with a molecular weight of 600. Polymers of this type can be formed by melt polymerization.

The biodegradable polymer matrix should make up 30 to 99.5% of the drug delivery composition by weight, preferably 65 to 99% by weight, more preferable 75 to 98% of the drug delivery composition by weight.

Any pharmaceutically active compound which is compatible with the biodegradable matrix can be used in this system. Preferred drugs are ophthalmologically active compounds. Examples of suitable drugs include ganciclovir, acyclovir, foscarnet, 5-fluorouracil, dexamethasone, Triamcinolone, prednisone, floxuridine, doxorobicin, daunorubicin, mitomycin, cytarabine, methotrexate and thioguanine.

The drug should be present in the drug delivery composition of 0.5 to 70% by weight, preferably 1–35% by weight and most preferably 2–25% by weight relative to the weight of the total composition.

The present invention is further illustrated by the following examples which illustrate the formulation and use of this invention. These examples are intended as illustrative and are not intended to limit the scope of the claimed invention.

EXAMPLE 1

Melt Polymerization of PEG600 with PCL2000 to create PLC2000-PEG600-PCL2000 Meltamer Mix 19.7 gm (0.033 moles) PEG-600 with 136.2 gm (0.068 moles) PCL-2000 in a round bottom flask at 50°–60° C. for 24 hours under 0.5 mmHg vacuum. Provide a by-product reservoir for the escaping water from the reaction. Recrystallize by dissolving the polymer into hot ethyl acetate (1st solvent) and filtering the solution through a Whatman No. 2 filter. Then add hexane (2nd solvent) dropwise to the warm filtrate until solution starts to become cloudy. Add enough of 1st solvent to make solution clear again. Allow the solution to cool (refrigeration overnight). Meltamer crystals form during cooling. Filter the cool solution and rinse crystals with cold, fresh 1st solvent. Dry crystals in warm (<50° C.) oven under partial (~0.5 mmHg) vacuum Yield was 69% after recrystallization.

EXAMPLE 2

Melt Polymerization of PEG400 with PCL1250 to create PCL1250-PEG400-PCL1250 Meltamer Mix 0.04 moles PEG-400 with 0.08 moles PCL-1250 in a round bottom flask at 50°–60° C. for 24 hours under 0.5 mmHg vacuum. Provide a by-product reservoir for the escaping water from the reaction. Recrystallize as described above. Yield was 74% after recrystallization. Other possible 1st solvents are: acetone, chloroform, dichloroethane, and toluene. Other possible 2nd solvents are: water, methanol, and ethanol.

General Analysis

In vitro meltamer degradation can be followed in water bath at 37° C. Load samples of each meltamer into syringes, heat them in oven at 55° C., and inject them into water at 37° C. Variable disappearance times (from 30 minutes to 3 days) are noted.

In vivo compatibility and degradation lifetimes in the eye can be ascertained by injecting the sterilized meltamer into both the anterior chamber (AC) and vitreous cavity of laboratory rabbits' eyes. Vitreous cavity degradation appears to be faster than AC degradation. Still, meltamer remains present in both cavities for over three months.

Chemical analysis includes determination of solubilities in common laboratory solvents, nuclear magnetic resonance and fourier transform infrared analyses to confirm chemical structure, and differential scanning calorimetric analysis to determine melting temperature. A summary of some differential scanning calorimetric results is shown in Table 1.

TABLE 1

| Melting Temperatures of Meltamers | |
|---|---|
| MELTAMER | MELTING TEMPERATURE (°C.) |
| PCL530-PEG1000-PCL530 | 25 |
| PCL530-PEG400-PCL530 | 30 |
| PCL530-PEG600-PCL530 | 38 |
| PCL1250-PEG400-PCL1250 | 42 |
| PCL1250-PEG1000-PCL1250 | 44 |
| PCL2000-PEG1000-PCL2000 | 48 |
| PCL2000-PEG400-PCL2000 | 48 |
| PCL1250-PEG600-PCL1250 | 49 |
| PCL2000-PEG600-PCL2000 | 52 |

Drug Incorporation into Meltamer

Drugs such as gancyclovir can be incorporated into the meltamer by first exposing both drug and meltamer to liquid nitrogen, then grinding them together. Drug percentages can range from 2.5 to 30 weight percent. The meltamer-drug composition can then be loaded into syringes for ethylene oxide sterilization for in vivo use.

While the invention has been described in connection with what is presently considered to be the most practical and preferred embodiment, it is to be understood that the invention is not limited to the disclosed embodiment, but, on the contrary, is intended to cover various modifications and equivalent arrangements included within the spirit and scope of the appended claims.

What is claimed is:

1. A drug delivery composition for injection into a body, comprising a pharmaceutically active agent and biodegradable polymer which are physically mixed together, wherein the polymer comprises from 30 to 99.5% by weight of said drug delivery composition, is solid at a temperature in the range 20° to 37° C. and flowable in the range of 38° to 52° C., and is a block co-polymer of formula:

A—B—A wherein A is a hydrophobic polymer or oligomer and B is a hydrophilic polymer or oligomer.

2. A drug delivery composition for injection into a body, comprising a pharmaceutically active agent physically mixed with a biodegradable block co-polymer of formula:

A—B—A wherein A is a hydrophobic polymer or oligomer and B is a hydrophilic polymer or oligomer;
   wherein the biodegradable block co-polymer comprises from 30 to 99.5% by weight of said drug delivery composition and is solid at a temperature in the range 20° to 37° C. and flowable in the range of 38° to 52° C.; and
   wherein A is selected from the group consisting of polyglycolic acid, polyethylene terephthalate, polybutyl lactone polycaprolactone, D-polylactic acid, L-polylactic acid, polyglutamic acid, poly L-lysine, and poly L-aspartic acid; and
wherein B is selected from the group consisting of polyethylene glycol, polypropylene glycol and polyvinyl alcohol.

3. A drug delivery composition according to claim 1, wherein A is selected from the group consisting of polyglycolic acid, polyethylene terephthalate, polybutyl lactone polycaprolactone, D-polylactic acid, L-polylactic acid, polyglutamic acid, poly L-lysine, and poly L-aspartic acid; and wherein B is selected from the group consisting of polyethylene glycol, polypropylene glycol and polyvinyl alcohol.

4. A drug delivery composition according to claim 1, wherein the biodegradable polymer is a polymer of formula:

$$H[O(CH_2)_5C]_n-[OCH_2CH_2]_m-[OC(CH_2)_5O]_n-H$$

wherein m is in the range 9.09 to 45.45 and n is in the range 6.16 to 45.45.

5. A drug delivery composition as claimed in claim 1, wherein the pharmaceutically active agent is selected from gancyclovir, 5-fluorouracil, acyclovir, dexamethasone, triamcinolone, prednisone, floxuridine, doxorubicin, daunorubicin, mitomycin, cytarabine, methotrexate and thioguanine.

6. A drug delivery composition according to claim 5 wherein the pharmaceutically active agent is selected from gancyclovir and 5-fluorouracil.

7. A drug composition according to claim 1, wherein the pharmaceutically active agent is present in the amount 0.5 to 70% by weight relative to the total weight of the composition.

8. A drug delivery composition according to claim 7, wherein the pharmaceutically active agent is present in an amount 1 to 35% by weight relative to the total weight of the composition.

9. A drug delivery composition according to claim 8, wherein the pharmaceutically active agent is present in an amount 2% to 25% by weight relative to the total weight of the composition.

10. A drug delivery composition according to claim 1 comprising a pharmaceutically active agent and biodegradable tri-block copolymer of the formula

A—B—A, wherein A is polycaprolactone with a molecular weight of 2000 and B is polyethylene glycol with a molecular weight of 600.

* * * * *